United States Patent [19]

Feuer et al.

[11] 4,166,862

[45] Sep. 4, 1979

[54] ANIMAL FEED CONTAINING ANABOLIC ISOFLAVONES

[75] Inventors: Laszlo Feuer; Mihály Nógrádi; Agnes Géttsegen; Borbala Vermes; János Strelisky; Andras Wolfner; Lorant Farkas; Sandor Antus; Maria K. Tóth, all of Budapest, Hungary

[73] Assignee: Chinoin Gyogyszer es Vegyeszeti Termekek Gyara Rt., Budapest, Hungary

[21] Appl. No.: 470,444

[22] Filed: May 16, 1974

Related U.S. Application Data

[63] Continuation-in-part of Ser. No. 146,773, May 25, 1971, Pat. No. 3,833,730.

[51] Int. Cl.$^2$ ............................................. A61K 31/35
[52] U.S. Cl. ................................................... 424/283
[58] Field of Search ............................... 424/263, 283; 260/345.2

[56] References Cited

U.S. PATENT DOCUMENTS 3,352,754 11/1967 Gazave ................................. 424/283
3,833,730 9/1974 Feuer ................................... 424/283

OTHER PUBLICATIONS

Rosenberg, Chem & Physiol. of the Vitamins, Interscience Pub., NY 1942, pp. 323–334, 337, 338, 515–518.

*Primary Examiner*—Anna P. Fagelson
*Attorney, Agent, or Firm*—Karl F. Ross

[57] ABSTRACT

An animal feed containing 0.00002 to 0.1% by weight of:
2-methyl-7-methoxy-4'-nitroisoflavone,
7-[hydroxyethoxy]-2-methylisoflavone,
7-carbethoxy-2-methylisoflavone,
7-ethoxyisoflavone,
7-n-benzyloxy-2-methylisoflavone,
7-p-nitrobenzyloxyisoflavone,
7-p-nitrobenzyloxy-2-methylisoflavone,
7-p-chlorobenzyloxyisoflavone,
7-cetyloxy-2-methylisoflavone,
7-(2-octyloxy)-isoflavone,
7-benzyloxy-3',4'-dimethoxyisoflavone, and
7-hexadecyloxyisoflavone
as a weight-gain promoting anabolic ingredient.

18 Claims, No Drawings

ANIMAL FEED CONTAINING ANABOLIC ISOFLAVONES

This application is a continuation-in-part of application Ser. No. 146,773, filed May 25, 1971 (Now U.S. Pat. No. 3,833,730) and is related to applications Ser. No. 371,560 filed June 19, 1973, now U.S. Pat. No. 3,907,830, and Ser. No. 374,056 filed June 27, 1973, now U.S. Pat. No. 3,864,362, both as continuations in part of application Ser. No. 146,773.

In order to reduce protein deficiency in nutrition or to terminate it thorough and significant research is being carried out throughout the world. One of the most obvious ways to achieve this objective is the use of additives to nutrients and feed, which improve the utilization of the nutrients introduced into the organism. In animal husbandry, these additives result in higher body-weight increase for an identical feed consumption and breeding period.

However, it has been rather difficult to develop an appropriate substance for increasing animal body weight since the use of substances with hormonal effects and of antibiotics is not permitted in most of the countries.

Isoflavone compounds have been subjected to a detailed investigation from the aspect of their body weight increasing effect. These compounds are rather widespread in plants, and a great number of them show oestrogenic properties. (cf. Virtanen, A. J.: Angew. Chem. 70, 544, (1958); Virtanen, A. J., Hietala, P. K.: Acta Chem. Scand. 12, 579 (1958). Grazing animals become infertile on consuming certain varieties of clover; research into this problem has shown that genistein and daidzein present in the plants consumed by pasturing animals are responsible for this effect because of their marked oestrogenic action (Chang, E. W. et al.: Ann. N.Y. Acad. Sci. 61, 625, (1955).

For the determination of the oestrogenic effect of isoflavones a reliable method has been evolved by East, J. (J. Endocrin. 13, 94, (1955). Since that time a number of authors have dealt very thoroughly with this problem (Matrone, G. et al.: Nutrition 59, 235, (1956); Gabor, M.: Naturwiss. 46, 650, (1959); Crabbe P. et al.: J. Am. Chem. Soc. 85, 5258, (1958).

The present invention relates to an animal feed containing as an active ingredient at least one compound of the formula

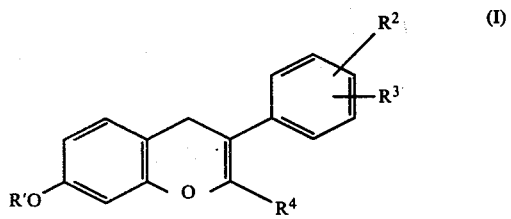

or a salt thereof, in which formula $R^1$ represents a substituted or unsubstituted, saturated or unsaturated alkyl, group, $R^2$ and $R^3$ represent hydrogen, an alkoxy, nitro, halogen, sulpho or hydroxy group, and $R^4$ is hydrogen, an alkyl or —COOH group. More specifically R' is isopropyl, benzyl or halobenzyl, R and $R^3$ are hydrogen or nitro and $R^4$ is hydrogen, methyl or carboxy.

Preferably the ingredient is a compound selected from the group which consists of 2-methyl-7-methoxy-4'-nitroisoflavone,
7-[hydroxyethoxy]-2-methylisoflavone,
7-carbethoxy-2-methylisoflavone,
7-(3-N-pyridyl)-propoxyisoflavone,
7-ethoxyisoflavone,
7-benzyloxy-2-methylisoflavone,
7-p-nitrobenzyloxyisoflavone,
7-p-nitrobenzyloxy-2-methylisoflavone,
7-p-chlorobenzyloxyisoflavone,
7-cetyloxy-2-methylisoflavone,
7-(2-octyloxy)-isoflavone,
7-benzyloxy-3', 4'-dimethoxyisoflavone, and
7-hexadecyloxyisoflavone The composition according to the present invention can be favorably applied as a feed additive. In that case one of the compounds of formula I, or a salt thereof, is added to the feed in amounts from 0.00002 to 0.1%, prior to or after the admixture of further additives.

The active ingredient according to the present invention may bear, if desired, also substituents on the alkyl group $R^1$. Substituents in this position may be a heterocycle, a dialkylamino group, a carbethoxy, hydroxyalkyl, alkoxy-alkyl or aryl or a substituted aryl group. The $R^1$ alkyl group may be substituted with a nitrogen containing heterocyclic group.

If desired, the compound is mixed with further additives. Substances with biological activity such as vitamins, aminoacids, choline chloride, salts of mineral acids, trace elements and other known substances of biological importance are suitable. The feed additive can be applied in premixes, in admixture with other components possessing biological effects. As further additives various diluents, solvents, sliding and molding substances, and carriers may be used. The feed additive can be mixed with the feed as a powder, granulate, powder mixture, emulsion or suspension. It is also possible to use the feed composition in mixtures added to the drinking water of the animals.

The new compounds can be made by a process wherein ketones of the formula

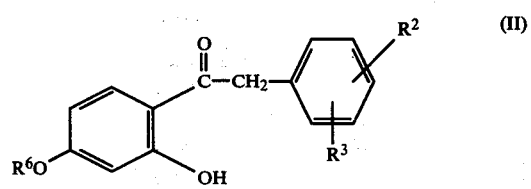

(a) are reacted with an alkyl orthoformate in the presence of a basic catalyst, or (b) are reacted with hydrogen cyanide and/or cyanides in the presence of hydrogen halide, or (c) are reacted with an alkyl formate in the presence of an alkali metal, or (d) are reacted with an alkyl oxalyl halogenide, followed, if desired, by saponification and/or decarboxylation of the obtained isoflavone ester, or (e) are reacted with an organic anhydride, or (f) are reacted with a N, N-dialkyl acid amide in the presence of phosphorus oxychloride, or whereby (g) 2-hydroxy-isoflavanone derivatives of the formula

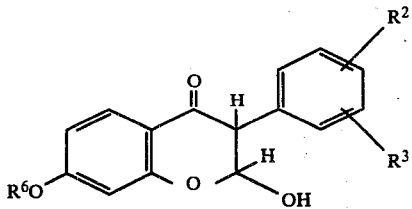

are dehydrated, and finally, if necessary, the $R^6$ group is converted into an $R^5$ group and/or the compounds are converted into salts or respectively, liberated from their salts, in the formulae $R^2$ and $R^3$ represent hydrogen, a halogen, alkoxy, nitro, sulpho or hydroxy group, $R^4$ is hydrogen, an alkyl or —COOH group, $R^5$ is an optionally substituted and/or unsaturated alkyl group with a carbon chain longer than two carbon atoms or carrying a substituent, and which alkyl group may also be unsaturated, $R^6$ is hydrogen, or, if desired, a substituted alkyl group or acyl group.

In carrying out variant (a) of the process according to the present invention the preferred method is to react an appropriately substituted ketone with an orthoformic ester in an aprotic solvent of higher boiling point. Pyridine, dimethyl formamide or diethyleneglycol dimethylether may be used as solvents, while preferably piperidine, morpholine, pyrrolidine and other secondary amines may serve as basic catalysts.

In carrying out variant (b), the preferred method is to react the ketones with hydrogen cyanide, in an aprotic solvent, in the presence of dry gaseous hydrochloric acid or of other hydrogen halides and Lewis acids, respectively. In this reaction, also aprotic solvents of non-basic nature, preferably diethylether or other dialkylethers can be applied. Zinc chloride or other Lewis acids may be used as catalysts. The reaction is carried out with hydrogen cyanide or with one of its appropriate salts, preferably with zinc cyanide. The mixture may be saturated with dry gaseous hydrochloric acid, and lastly, the formed substituted α-formimino-2-hydroxyphenyl-benzyl-ketone hydrochlorides are decomposed by treatment with water.

In carrying out variant (c) of the process according to the invention, ketones of the formula

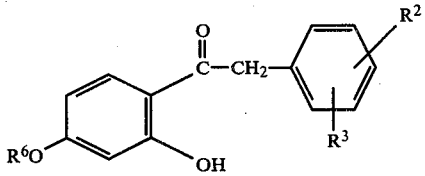

are reacted with alkyl formates in the presence of an alkali metal. A preferred method is to dissolve an appropriately substituted 2-hydroxy-phenyl-benzyl-ketone in ethyl formate, and adding the solution dropwise to powdered sodium metal, then decomposing the reaction mixture with water, and separating the formed isoflavone.

According to variant (d) of the process according to the present invention appropriately substituted 2-hydroxy-phenyl-benzyl ketones are reacted with alkyl oxalyl halides. The formed 2-carbalkoxy-isoflavone derivative can be converted, if desired, into an isoflavone derivative unsubstituted in position 2, by hydrolysis of the ester group followed by decarboxylation. This process can be carried out preferably with methyl or ethyl oxalyl chloride in the presence of a basic acid-binding agent in an appropriate aprotic solvent (such as preferably pyridine or another tertiary amine capable of binding acids).

According to variant (e) of the process according to the invention, the appropriately substituted 2-hydroxyphenyl-benzyl ketone is reacted with organic acid anhydrides in the presence of a basic catalyst. The anhydrides of acetic, propionic or benzoic acids can be used as organic acid anhydrides. The anhydride is heated in the presence of a basic catalyst, preferably of the alkali metal salt of the acid component of the anhydride or of a tertiary amine, in the absence of solvents or in an aprotic solvent of higher boiling point such as pyridine or dimethyl formamide.

On carrying out variant (f) of the process according to the invention, the ketone is reacted with N,N-dialkyl acid amides in the presence of phosphorus oxychloride, preferably in a way that the appropriately substituted 2-hydroxy-phenyl-benzyl ketone is heated with the N,N-dialkyl acid amide (dimethyl formamide, dimethyl acetamide) and phosphorus oxychloride, and using the N,N-dialkyl acid amide itself as a solvent.

In carrying out variant (g) of the process according to the invention, 2-hydroxy-isoflavanones of the formula IV are dehydrated by heating alone or in an acidic medium in a polar solvent.

In the course of the process according to the present invention, in the first step, from the compounds of the formula III or IV, derivatives can be obtained in which the substituent $R^6$ is not the $R^5$ group desired to be present in the end product. In these cases the $R^6$ group may be converted into an $R^5$ group. This operation can be carried out by the partial or complete alkylation of mono- and poly-hydroxy-isoflavones, respectively. The alkylation can be preferably performed with alkyl or substituted alkyl halides, alkyl sulphates, olefins and epoxides, preferably in a way that the mentioned alkylating agents are heated with the isoflavones to be alkylated, in appropriate solvents, ketones, dimethyl formamide or ethers having a longer carbon chain, in the case of haloid compounds preferably in the presence of an acid-binding agent such as an alkali carbonate, and in the case of alkyl bromides and alkyl chlorides preferably in the presence of an alkali iodide as additive.

The mentioned operation can also be carried out by the partial or complete deacylation and, respectively, the partial or complete dealkylation of acyloxy- and polyacyloxy-, alkyloxy- and polyalkyloxy-isoflavones. Acyloxy- and polyacyloxy isoflavones are formed when the procedure according to variant (e) is carried out with di- and polyhydroxy-phenyl-benzyl ketones, respectively, carrying a 2-positioned hydroxy group. Deacylation is preferably performed in an acidic or alkaline medium in the presence of a polar solvent.

The operation can also be performed by the decarboxylation of isoflavone-2-carboxylic acids. Isoflavone-2-carboxylic acids are formed in variant (d) of the process according to the invention and their decarboxylation may be preferably carried out by heating them in the presence of catalysts such as powdered copper or in the absence of catalysts.

On the basis of the abundant literature on studies concerning the oestrogenic properties of isoflavones, and of the data of our research in this field, we were able to produce isoflavone compounds as described which are devoid of any oestrogenic effects. According to the present invention, the compounds
2-methyl-7-methoxy-4'-nitroisoflavone,
7-[hydroxyethoxy]-2-methylisoflavone,
7-carbethoxy-2-methylisoflavone,
7-(3-N-pyridyl)-propoxyisoflavone,
7-ethoxyisoflavone,
7-n-benzyloxy-2-methylisoflavone,
7-p-nitrobenzyloxyisoflavone,
7-p-nitrobenzyloxy-2-methylisoflavone,
7-p-chlorobenzyloxyisoflavone,
7-cetyloxy-2-methylisoflavone,
7-(2-octyloxy)-isoflavone,
7-benzyloxy-3', 4'-dimethoxyisoflavone, and
7-hexadecyloxyisoflavone
show a marked weight-gain increasing effect which essentially exceeds that of isoflavone compounds possessing definitely oestrogenic effects, and this weight-gain increasing effect is associated with a reduction or complete absence of oestrogenic effects.

Thus, in the course of our observations in discovering in a field still not described in literature, i.e. in the group non-oestrogenic isoflavones, a very interesting novel biological effect, that of increasing the weight yield has been found. Beside this action, the compound possesses an anatoxic effect free of androgen effects as well (proved by N-retention and by the musculus levator test or by measuring the skeletal muscle increasing effect).

Certain compounds described in this disclosure are also suitable for other applications in animal husbandry such as for increasing the yield of milk, egg and wool, for the improvement of the economy of fish production in fisheries, as well as in the breeding of fur-farm animals, in game economy etc.

Concerning the effect of the compounds the pharmacological tests given below are of special interest.

Test of anabolic effect: The investigation was carried out with castrated rats by means of the musculus levator ani test and vesicula seminalis test. The preparations were administered orally for a period of three weeks. The tests were performed by the method of Eisenberg and Gordan (Eisenberg, E., Gordan, G. S. J.: J. Pharmacol. 99, 38 (1950). In addition, also the weight of the prepared diaphragm of the animals was established. According to these tests, the weight of musculus levator ani rose by a Student significance of p 0.01, the weight of vesicula seminalis did not increase while the weight of the prepared diaphragm of the animals increased by a Student significance of p 0.05. On the basis of these results the preparations proved to be anabolic and free of androgen effect.

During the tests, a total of 30 mg/kg of active ingredient was administered to the animals.

The investigation of nitrogen retention was carried out also with rats. Under a systematic treatment, the nitrogen excretion of the treated animals decreased on the 20th and 30th day, respectively, by a significance of p 0.05.

The results of these investigations similarly points to the anabolic effect.

Exeminations with S-35 labelled methionine showed that with treatment, increased methionine incorporation takes place in the muscle tissues of the treated animals.

The muscle-activity-increase was investigated by the forced swimming test of rats. The animals were forced to swim in water of 29° C. with a load of 3 g/100 g body weight. The calorie content and quantity of feed administered was the same as with control animals.

The difference between the periods of forced swimming until exhaustion of the control animals and the animals treated for 45 days and forced to swim daily was 33 minutes (the control animals were subjected to identical treatment with the exception of the active ingredient), i.e. the swimming period (performance) of the control animals increased from 166 to 196 minutes while that of the treated animals from 162 to 225 minutes.

These experiments were carried out by administering daily doses of 5 mg/kg of body weight.

In further experiments we succeeded in partially suppressing the anticatabolic effect of cortisone with the compound.

On examining the data of the analysis of body weight it was found that the weight increase of the muscle tissue was specifically greater than that of the fat tissue, and that fat content of the muscle tissue decreased, while that of proteins rose.

The acute toxicity tests proved the full inocuity of the preparation. During a 48 hour period of observation no mice died on administering orally 4000 mg/kg of body weight doses or subcutaneously 3500 mg/kg doses. In rat tests, no perceptible alterations were observed during a 48 hour period, after administering orally or subcutaneously 3500 mg/kg of body weight doses.

On dogs, no alterations were observed during a week of administering 3500 mg/kg body weight doses.

The subacute toxicity tests were performed on rats. When administering daily doses of 200 mg/kg of body weight and 500 mg/kg of body weight orally, no alterations could be observed after one month of test period.

Similar results were obtained in the subacute tests carried out with mice.

As regards to chronic toxicity up to the present, the three-month chronic toxicity tests have been completed. After administering daily 100 mg/kg of body weight and 10 mg/kg of body weight doses for three months to male and female rats, no perceptable alterations were observed (full blood investigation, histological and other clinical tests).

Similarly negative results were obtained in the toxicity test with dogs after the first 3 months of observation (here the applied doses were 20 mg/kg of body weight and 50 mg/kg of body weight).

The oestrogenic effect of the compounds was investigated by the uterus test on infantile mice, after oral and subcutaneous administration. No oestrogenic effects were observed.

After administering daily 5 mg/kg of body weight of preparations to chickens for 30 days, the endocrine glands of the experimental animals were subjected to a detailed histological investigation. No perceivable alterations were observed.

The weight-gain increasing effect induced by doses of 2 g/100 kg of feed was in the various animal species as follows:
8 to 15% in calves
7 to 10% in cattle
7 to 10% in hogs
8 to 20% in poultry
10 to 20% in rabbits
8 to 12% in guinea pigs The periods of administration varied from one to four months, depending on the animal species and conditions of breeding. The treated animals did not obtain greater amounts of feed than the control tests during the treatment period. Moreover, in several cases some saving of feed was attained in spite of the weight-gain increasing effect.

It was observed during the treatment period that the experimentally treated animals showed an increased vitality, and that the weight increase was mainly due to an increase of the muscle mass. This was particularly evident in pig fattening trials when in case of bacon pigs the ratio of pigs of class A, low in fat, was significantly higher.

In rats, also the effect exerted on the reproductive organs was separately examined. The capability of reproduction and the number of brood were in case of males and females pretreated with the active ingredient the same as that on untreated controls.

In an investigation on the uptake and excretion of C-14 labelled isoflavones it was found that the uptake is rather quick both in case of oral and of intramuscular administration, half of the ingredient introduced was excreted with urine while the other half with faeces.

In a number of organs, activity detectable by radiography was present 48 hours after completion of the treatment.

EXAMPLE 1

27 g of 2-hydroxy-4-isopropyloxy-phenyl-benzyl ketone, 22 g of ethyl orthoformate and 5 g of morpholine are boiled for 8 hours in 200 ml of dimethyl formamide. The ethanol formed during the reaction is removed through a fractionation head. Then the major part of solvent is distilled off in a vacuum and the residue is diluted with dilute aqueous hydrochloric acid. The crude product is filtered and recrystallized from acetone, yielding 24 g of 7-isopropyloxy-isoflavone of m.p. 115°–117° C.

On applying a similar method, 7-n-butyloxy-isoflavone, m.p. 152°–153° C., can be prepared from 4-n-butyloxy-2-hydroxy-phenyl-benzyl-ketone (m.p. 71°–73° C.), and 7-n-amyloxy-isoflavone, m.p. 142°–143° C. from 4-n-amyloxy-2-hydroxy-phenyl-benzyl ketone (m.p. 72°–75° C.).

EXAMPLE 2

28.6 g of 2-hydroxy-4-n-butyloxy-phenyl-benzyl ketone are dissolved in 50 ml of anhydrous ether, 25 g of zinc cyanide are added, and the solution is saturated, under cooling, with dry hydrogen chloride gas. After allowing the mixture to stand for 24 hours, the solvent is decanted from the separated oil, the oil triturated with ether, the ether is decanted, and the residue is heated with 1000 ml of water for 30 minutes on a water bath. The product which precipitates on cooling is filtered, and recrystallized from a mixture of methanol and acetone, thus 15 g of 7-n-butyloxy-isoflavone are obtained.

7-Isopropyloxy-isoflavone and 7-n-amyloxy-isoflavone already described in Example 1 can be produced in a similar way.

EXAMPLE 3

A solution of 18 g of 2-hydroxy-4-isopropyloxy-phenyl-benzyl ketone in 150 g of ethyl formate is added in small portions under cooling to 9 g of powdered sodium. After allowing the reaction mixture to stand for some hours, it is treated with ice water containing hydrochloric acid, the ethyl formate is distilled off, the residual aqueous mixture is boiled for an hour, and the product precipitated on cooling is recrystallized from acetone, thus 11 g of 7-isopropyloxy-isoflavone are obtained, m.p. 115°–117° C. In a similar way, 7-n-butyloxy-isoflavone and 7-n-amyloxy-isoflavone already described in Example 1 can also be produced.

EXAMPLE 4

To a solution of 13.5 g of 2-hydroxy-4-isopropyloxy-phenyl-benzyl ketone in 120 ml of pyridine, 11 ml of ethyloxalyl chloride are added under cooling. After allowing the reaction mixture to stand for a day, it is diluted with water, extracted with chloroform and repeatedly shaken with a 10% aqueous hydrochloric acid solution. On evaporating the solution, the residue is treated for 5 hours with a mixture of 100 ml of methanol and 50 ml of a 10% aqueous solution of sodium hydroxide, the methanol is distilled off, and the aqueous solution is acidified. The product is filtered, thoroughly dried and, after addition of 5 g of powdered copper, heated to 250° C. On completion of the evolution of gas, the residue is crystallized from methanol, yielding 5 g of 7-isopropyloxy-isoflavone, m.p. 116°–117° C.

EXAMPLE 5

28.6 g of 2-hydroxy-4-n-butyloxy-phenyl-benzyl ketone and 25 g of anhydrous sodium acetate are boiled for 14 hours with 120 ml of acetic anhydride under a reflux condenser. The reaction mixture is poured into water, allowed to stand and the precipitated substance is recrystallized from a mixture of methanol and acetone, yielding 25 g of colorless crystals of 7-n-butyloxy-2-methyl-isoflavone, m.p. 91°–93° C. In a similar way, 7-isopropyloxy-2-methyl-isoflavone, m.p. 152°–154° C.; 7-n-amyloxy-2-methyl-isoflavone, m.p. 87°–89° C., and 2-methyl-3',4',5,7-isoflavone, m.p. 214°–215° C. can also be produced.

EXAMPLE 6

16 g of phosphorus oxychloride are mixed with 50 ml of dimethyl formamide with cooling. After 15 minutes, 27 g of 2-hydroxy-4-isopropyloxy-phenyl-benzyl ketone are added, and the mixture is boiled for 18 hours under reflux condenser. On dilution with water, the precipitate is filtered, dried, boiled with 200 ml of methanol, and the methanolic extract is evaporated to a small volume. On recrystallizing the separated crude product from acetone, 10 g of 7-isopropyloxy-isoflavone described in Example 1 are obtained.

EXAMPLE 7

23.8 g of 7-hydroxy-isoflavone in 200 ml of anhydrous acetone are boiled, under stirring, with 18 g of n-hexyl bromide, 18 g of potassium carbonate and 1 g of potassium iodide for 72 hours under reflux condenser. The inorganic salts are removed by filtration, the filtrate is subjected to steam distillation in order to remove acetone and excess reagent, the precipitate is filtered and recrystallized from acetone, yielding 20 g of 7-n-hexyloxy-isoflavone, m.p. 120°–122° C. In a similar way, also 7-isopropyloxy-isoflavone, 7-n-butyloxy-isoflavone, and 7-n-amyloxy-isoflavone already characterized in Example 1, 7-isopropyloxy-2-methyl-isoflavone, 7-n-butyloxy-isoflavone and 7-n-amyloxy-isoflavone already characterized in Example 5, and
7-n-propyloxy-isoflavone, m.p. 162°–164° C.,
7-n-propyloxy-2-methyl-isoflavone, m.p. 120°–122° C.,
7-n-hexyloxy-2-methyl-isoflavone, m.p. 62°–64° C.,
7-benzyloxy-2-methyl-isoflavone, m.p. 139°–141° C., 7-(4-chlorobenzyloxy)-isoflavone, m.p. 182°–184° C.,
7-(4-chlorobenzyloxy)-2-methyl-isoflavone, m.p. 154°–156° C.,
7-(4-nitrobenzyloxy)-2-methyl-isoflavone, m.p. 201°–203° C.,
7-carbethoxy-methoxy-3',4'-dimethoxy-isoflavone, m.p. 149°–152° C.,
7-carbethoxy-methoxy-3',4'-dimethoxy-2-methyl-isoflavone, m.p. 132°–134° C.,
7-(2-ethoxy-ethoxy)-isoflavone, m.p. 139°–140° C.,
7-(2ethoxy-ethoxy)-2-methyl-isoflavone, m.p. 104°–105° C.,
7-(2-ethoxy-ethoxy)-3',4'-dimethoxy-2-methyl-isoflavone, m.p. 132°–133° C.,
7-(2-hydroxy-ethyoxy)-isoflavone, m.p. 144°–146° C.,
7-(2-hydroxy-ethoxy)-2-methyl-isoflavone, m.p. 151°–153° C.,
7-(2-hydroxy-ethoxy)-3',4'-dimethoxy-isoflavone, m.p. 145°–156° C., and
7-(3-chloropropyloxy)-isoflavone, m.p. 137°–138° C. can be prepared.

EXAMPLE 8

12 g of 7-hydroxy-isoflavone are boiled for 2 hours under reflux condenser with 10 g of potassium carbonate and 9 g of sec-butyl bromide in 40 ml of dimethyl formamide. On pouring the reaction mixture on water, the separated product is recrystallized from acetone, yielding 12 g of 7-sec-butyloxy-isoflavone, m.p. 87°–89° C. In a similar way, also 7-sec-butyloxy-2-methyl-isoflavone, m.p. 107°–109° C., and all the other isoflavone derivatives described in Example 7 can be prepared.

EXAMPLE 9

10 g of 5,7-diacetoxy-2-methyl-isoflavone of m.p. 177°–178° C. prepared by the method described in Example 5 are boiled for 10 minutes with 50 ml of methanol and with a solution of 5 g of sodium hydroxide in 30 ml of water. On acidifying the solution with a 10% aqueous sulphuric acid, the precipitated product is filtered, affording 6 g of 5,7-dihydroxy-2-methyl-isoflavone, m.p. 228°–229° C.

EXAMPLE 10

Formulation of poultry raising feed:

| | |
|---|---|
| Maize | 40.0 kg |
| Feed wheat | 20.0 kg |
| Bran | 6.0 kg |
| Extracted soybeans | 13.0 kg |
| Extracted groundnut | 11.5 kg |
| Powdered alfalfa | 1.4 kg |
| Extracted sunflower seed | 4.0 kg |
| Potassium-phosphorus composite "Foszkal" | 0.5 kg |
| Feed lime | 2.3 kg |
| Feed sodium chloride | 0.3 |
| Vitamin premix 2 | 0.5 kg |
| Mineral premix II | 0.5 kg |
| Total: | 100.0 kg |

+2 g of 7-isopropyloxy-isoflavone/100 kg of feed.

EXAMPLE 11

Formulation of pig feed:

| | |
|---|---|
| Bran | 22.0 kg |
| Extracted soybeans | 15.0 kg |
| Extracted groundnut | 6.0 kg |
| Powdered linseed | 14.0 kg |
| Powdered alfalfa | 4.0 kg |
| Powdered milk | 15.0 kg |
| Fish meal | 10.0 kg |
| Yeast | 2.0 kg |
| Feed lime | 6.0 kg |
| Feed soidum chloride | 1.5 kg |
| Vitamin premix | 3.0 kg |
| Mineral premix | 1.5 kg |
| Total: | 100.0 kg |

+2 g of 7-isopropyloxy-isoflavone/100 kg of feed.

EXAMPLE 12

10 g of 7-hydroxy-2-methyl-isoflavone, 10 g of anhydrous potassium carbonate, 1 g of potassium iodide and 12.5 g of benzyl chloride are boiled in 200 ml of anhydrous acetone for 2 hours with stirring, under a reflux condenser. On subjecting the mixture to steam distillation, the crude product precipitating from the water is filtered, dried, and recrystallized from a mixture of 100 ml of methanol and 40 ml of acetone, affording white needle crystals of 7-benzyloxy-2-methyl-isoflavone, m.p. 139°–141° C.

EXAMPLE 13

(a) To a solution of 12 g of 2-hydroxy-4-methoxyphenyl-benzyl ketone in 120 ml of anhydrous pyridine, 11 ml of ethoxalyl chloride are added dropwise, with stirring and cooling. After standing overnight, the mixture is poured onto water, extracted with chloroform, washed with 10% hydrochloric acid until free of pyridine, then with water until it is free of acid. After drying and evaporation an oil, 7-methoxy-2,3-dihydro-isoflavone-2-ol-2-carboxylic ethylester is obtained which is subsequently heated with 120 ml of glacial acetic acid and 12 ml of concentrated hydrochloric acid for half an hour on a water bath. On cooling and pouring onto water, 2-carbethoxy-7-methoxy-isoflavone precipitates. Recrystallized from methanol, m.p. 130°–132° C.

(b) 13 ml of 2 N sodium hydroxide are added to a solution of 8.25 g of the ester obtained in paragraph (a) in 240 ml of acetone, and the mixture is stirred for 5 hours. After removing the major part of acetone, the residue is acidified with 10% hydrochloric acid. Addition of some water precipitated snow-white 7-methoxy-isoflavone-2-carboxylic acid which was separated. M.p. 241°–243° C. (with decomposition).

EXAMPLE 14

10.5 g of 7-hydroxy-isoflavone in 200 ml of anhydrous acetone are boiled for 2 hours with 11.8 g of p-nitrobenzyl iodide in the presence of 5.7 g of anhydrous potassium carbonate under reflux condenser. On distilling off about half of the volume of acetone, the residue is poured onto 1000 ml of water. The precipitating crude product is subjected to suction and recrystallized from glacial acetic acid, affording light yellow plates of 7-p-nitrobenzyloxy-isoflavone, m.p. 225°–226° C.

Test results for anabolic isoflavone derivative

Test animals: chicks
Composition of the poultry starter feed
  Corn=60%; Soy (45%) 20%; Corn meal 2%; Fishmeal (65%) 10%; Yeast 3.3%; Calcium phosphate 0.6%; Calcium 2.3%; Salt 0.3%; Vitamin mixture I 1.0%; Mineral mixture I 0.5%.

Content:
    Dry 86%; Starch (kg/100 kg) 69.5; Raw eggwhite 19.5%; Digestible raw eggwhite 17.1%.
Composition of the poultry maintenance feed:
    Corn 50%; Wheat 14.9%; Soy (45%) 12.5%; Hazel nut bits 9%; Corn meal 2.0%; Fish meal (65%) 4.5%; Meat meal (45%) 3.0%; Calcium phosphate 1.0%; Calcium 1.8%; Salt 0.3%; Vitamin mixture II 0.5%; Mineral mixture I 0.5%.
Content:
    Dry 86%; Starch (kg/100 kg) 69.5; Raw egg white 19.5%; Digestible raw egg white 17.1%.
Composition of the vitamin mixtures

|  | Vitamin mixture I. 0.5% | Vitamin mixture II. 0.5% |
|---|---|---|
| A-Vitamin | 2,000,000 IU | 1,200,000 IU |
| D-3 Vitamin | 400,000 IU | 300,000 IU |
| E-Vitamin | 4,000 IU | 2,000 IU |
| K-3 Vitamin | 400 mg | 400 mg |
| B-1 Vitamin | 400 mg | 200 mg |
| B-2 Vitamin | 800 mg | 700 mg |
| B-3 Vitamin | 1,200 mg | 2,000 mg |
| B-6 Vitamin | 400 mg | 500 mg |
| B-12 Vitamin | 10 mg | 4 mg |
| Niacin | 4,000 mg | 5,000 mg |
| Cholinchloride | 100,000 mg | 100,000 mg |
| Bacitracin | 6,000 mg | 4,000 mg |
| Ethoxy-methyl-quinoline | 25,000 mg | 25,000 mg |
| Furazolidon | 20,000 mg | —mg |
| Ardinon | — | 25,000 mg |

Composition of mineral mixture I

| Manganese | 20,000 mg |
|---|---|
| Iron | 2,000 mg |
| Zinc | 8,000 mg |
| Copper | 400 mg |
| Iodine | 150 mg |
| Ethoxy-methyl-quinoline in 100,000 g bran. | 100 mg |

The material is used as a starter feed and as a maintenance feed in a concentration of 2 g/100 kg feed. The mixing is carried out in two steps: a first mixing to obtain a concentration of 1000 ppm and a second mixing to 20 ppm.

After the mixing the concentration was tested qualitatively as a control.

During the tests the temperature and humidity of the atmosphere was held constant. The length of the tests was 4–5 weeks and the weight of the chicks was checked once a week. In the first week the animals were given the starter feed, in the second week starter feed and maintenance feed in equal portions, and from the third week pure maintenance feed.

The results of the tests with the chicks are assembled in the following Table:

|  | No. of animals Number | Age of the animals at the start of the tests Day | Length of the treatment Weeks | Starting weight averages g | Final weight averages g | Weight change % over control + | Feed rating % |
|---|---|---|---|---|---|---|---|
| 2-Methyl-7-methoxy-4'-nitro-isoflavone | 20 | 7 | 4 | 95 | 469 | +6.3 | 94.5 |
| 7-[2-Hydroxyethoxy-]-2-methyl-isoflavone | 20 | 7 | 4 | 95 | 470 | +6.4 | 94.1 |
| 7-Carbethoxy-2-methyl-isoflavone | 20 | 7 | 4 | 95 | 450 | +1.8 | 98.6 |
| Control group | 20 | 7 | 4 | 95 | 442 | — | — |
| 7-3-(N-Pyridyl)-propoxy-isoflavone | 20 | 3 | 4 | 41 | 353 | +3 | 98 |
| 7-Ethoxy-isoflavone | 20 | 3 | 4 | 41 | 353 | +6 | 95 |
| 7-Isopropoxy-isoflavone | 20 | 3 | 4 | 42 | 374 | +9 | 93 |
| Control group | 20 | 3 | 4 | 41 | 343 | — | — |
| 7-n-Benzyloxy-2-methyl-isoflavone | 20 | 5 | 4 | 49 | 390 | +8 | 92 |
| 7-p-Nitrobenzyloxy-isoflavone | 20 | 5 | 4 | 49 | 386 | +7 | 94 |
| 7-p-Nitrobenzyloxy-2-methyl-isoflavone | 20 | 5 | 4 | 49 | 372 | +3 | 98 |
| 7-p-Chlorobenzyloxy-isoflavone | 20 | 5 | 4 | 49 | 372 | — | — |
| Control group | 20 | 5 | 4 | 49 | 361 | — | — |
| 7-Cetyloxy-2-methyl-isoflavone | 20 | 7 | 4 | 100 | 509 | +5.1 | 97 |
| Control group | 20 | 7 | 4 | 99 | 485 | — | — |
| 7-Benzyloxy-3', 4'-dimethoxy-isoflavone | 20 | 7 | 5 | 96 | 1087 | +9.4 | 95.5 |
| Control group | 20 | 7 | 5 | 98 | 993 | — | — |
| 7-(2-Octyloxy)-iso- |  |  |  |  |  |  |  |

-continued

|  | No. of animals Number | Age of the animals at the start of the tests Day | Length of the treatment Weeks | Starting weight averages g | Final weight averages g | Weight change % over control + | Feed rating % |
|---|---|---|---|---|---|---|---|
| flavone | 30 | 10 | 5 | 112 | 1023 | +2.2 | 98.5 |
| 7-Hexadecyloxy-isoflavone | 30 | 10 | 5 | 112 | 1020 | +2.2 | 98.6 |
| Control group | 30 | 10 | 5 | 113 | 1001 | — | — |

We claim:

1. An animal feed containing 0.00002 to 0.1% by weight of 2-methyl-7-methoxy-4'-nitroisoflavone as a weight-gain-promoting anabolic ingredient.

2. An animal feed containing 0.00002 to 0.1% by weight of 7-(hydroxyethoxy)-2-methylisoflavone as a weight-gain-promoting anabolic ingredient.

3. An animal feed containing 0.00002 to 0.1% by weight of 7-carbethoxy-2-methylisoflavone as a weight-gain-promoting anabolic ingredient.

4. An animal feed containing 0.00002 to 0.1% by weight of 7-benzyloxy-2-methylisoflavone as a weight-gain-promoting anabolic ingredient.

5. An animal feed containing 0.00002 to 0.1% by weight of 7-p-nitrobenzyloxyisoflavone as a weight-gain-promoting anabolic ingredient.

6. An animal feed containing 0.00002 to 0.1% by weight of 7-p-nitrobenzyloxy-2-methylisoflavone as a weight-gain-promoting anabolic ingredient.

7. An animal feed containing 0.00002 to 0.1% by weight of 7-p-chlorobenzyloxyisoflavone as a weight-gain-promoting anabolic ingredient.

8. An animal feed containing 0.00002 to 0.1% by weight of 7-cetyloxy-2-methylisoflavone as a weight-gain-promoting anabolic ingredient.

9. An animal feed containing 0.00002 to 0.1% by weight of 7-benzyloxy-3',4'-dimethoxyisoflavone as a weight-gain-promoting anabolic ingredient.

10. In a method of feeding animals the improvement which comprises adding to the animal feed 0.00002 to 0.1% by weight of 2-methyl-7-methoxy-4'-nitroisoflavone as a weight-gain-promoting anabolic ingredient.

11. In a method of feeding animals the improvement which comprises adding to the animal feed 0.00002 to 0.1% by weight of 7-hydroxy-ethoxy-2-methylisoflavone as a weight-gain-promoting anabolic ingredient.

12. In a method of feeding animals the improvement which comprises adding to the animal feed 0.00002 to 0.1% by weight of 7-carbethoxy-2-methyl-isoflavone as a weight-gain-promoting anabolic ingredient.

13. In a method of feeding animals the improvement which comprises adding to the animal feed 0.00002 to 0.1% by weight of 7-benzyloxy-2-methylisoflavone as a weight-gain-promoting anabolic ingredient.

14. In a method of feeding animals the improvement which comprises adding to the animal feed 0.00002 to 0.1% by weight of 7-p-nitrobenzyloxy-isoflavone as a weight-gain-promoting anabolic ingredient.

15. In a method of feeding animals the improvement which comprises adding to the animal feed 0.00002 to 0.1% by weight of 7-p-nitrobenzyloxy-2-methyl-isoflavone as a weight-gain-promoting anabolic ingredient.

16. In a method of feeding animals the improvement which comprises adding to the animal feed 0.00002 to 0.1% by weight of 7-p-chlorobenzyloxyisoflavone as a weight-gain-promoting anabolic ingredient.

17. In a method of feeding animals the improvement which comprises adding to the animal feed 0.00002 to 0.1% by weight of 7-cetyloxy-2-methylisoflavone as a weight-gain-promoting anabolic ingredient.

18. In a method of feeding animals the improvement which comprises adding to the animal feed 0.00002 to 0.1% by weight of 7-benzyloxy-3',4'-dimethoxyisoflavone as a weight-gain-promoting anabolic ingredient.

* * * * *